(12) United States Patent
Plaian et al.

(10) Patent No.: US 11,129,531 B2
(45) Date of Patent: Sep. 28, 2021

(54) OPHTHALMIC MACHINE FOR ACQUIRING FLUORESCENCE IMAGES OF THE RETINA AND RELATED METHOD OF USE

(71) Applicant: CENTERVUE S.P.A., Padua (IT)

(72) Inventors: Andrei Plaian, Noventa Padovana (IT); Irene Mogentale, Due Carrare (IT); Frederico Manzan, San Pietro di Feletto (IT); Marco D'Aguanno, Padua (IT)

(73) Assignee: CenterVue S.p.A., Padua (IT)

( * ) Notice: Subject to any disclaimer, the term of this patent is extended or adjusted under 35 U.S.C. 154(b) by 464 days.

(21) Appl. No.: 16/306,667

(22) PCT Filed: Jun. 21, 2017

(86) PCT No.: PCT/EP2017/065317
§ 371 (c)(1),
(2) Date: Dec. 3, 2018

(87) PCT Pub. No.: WO2018/001838
PCT Pub. Date: Jan. 4, 2018

(65) Prior Publication Data
US 2019/0343384 A1    Nov. 14, 2019

(30) Foreign Application Priority Data

Jun. 28, 2016 (IT) .............................. 102016066840

(51) Int. Cl.
*A61B 3/12* (2006.01)
*A61B 3/00* (2006.01)
(Continued)

(52) U.S. Cl.
CPC .......... *A61B 3/1241* (2013.01); *A61B 3/0025* (2013.01); *A61B 3/156* (2013.01); *A61B 5/4088* (2013.01); *A61B 3/0008* (2013.01)

(58) Field of Classification Search
CPC ....... A61B 3/0008; A61B 3/0025; A61B 3/10; A61B 3/12; A61B 3/1241; A61B 3/156; A61B 5/4088
See application file for complete search history.

(56) References Cited

U.S. PATENT DOCUMENTS

| 6,088,606 A | 7/2000 | Ignotz et al. |
| 6,456,787 B1 | 9/2002 | Matsumoto et al. |

(Continued)

*Primary Examiner* — Amelie R Davis
(74) *Attorney, Agent, or Firm* — Patterson Intellectual Property Law, P.C.; Gary L. Montle

(57) ABSTRACT

An ophthalmic machine is provided for obtaining and diagnosing fluorescence images of the retina. An excitation light having first wavelengths (e.g., between 430 nm and 490 nm) is scanned onto the retina. Light emitted by the retina, when illuminated thereby, is filtered to block light of the first wavelengths and to pass light of second (higher) wavelengths. A second filter selects a component of the passed light having second (e.g., green) wavelengths, and a third filter selects a component of the passed light having third (e.g., red) wavelengths. First and second detection means receive light transmitted by the first and second filters, respectively, and provide detection signals indicative thereof. The detection signals are processed to provide one or more images of the retina, said images of the retina comprising at least a color fluorescence image of the retina.

15 Claims, 4 Drawing Sheets

Figure 1:
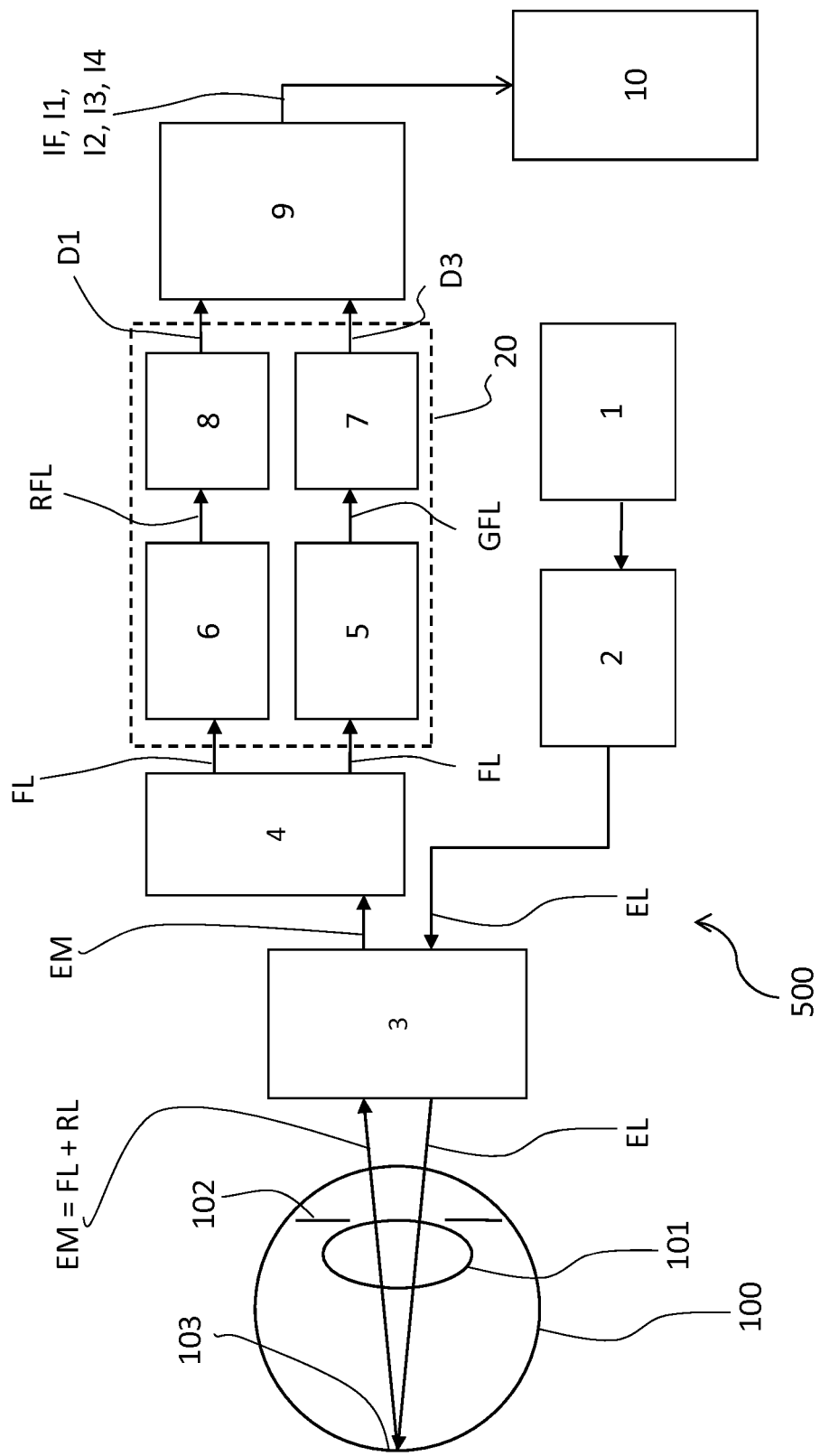

(51) Int. Cl.
*A61B 3/15* (2006.01)
*A61B 5/00* (2006.01)

(56) References Cited

U.S. PATENT DOCUMENTS

2004/0245350 A1 12/2004 Zeng
2015/0374232 A1 12/2015 Yoshino
2016/0106311 A1 4/2016 Smith

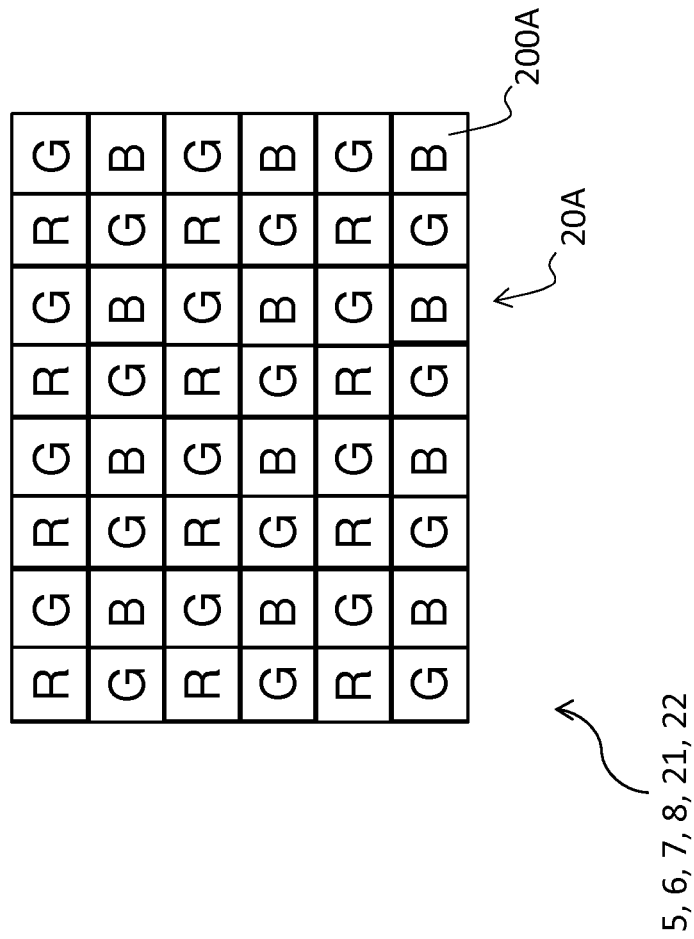

OPHTHALMIC MACHINE FOR ACQUIRING FLUORESCENCE IMAGES OF THE RETINA AND RELATED METHOD OF USE

The present invention relates to an ophthalmic machine for acquiring images of the retina, in particular of color fluorescence images of the retina.

As is known, the retina of the eye is naturally provided with various types of molecules with fluorescence properties (known as "fluorophores") characterized by bands of light excitation and of light emission that differ from one another.

It is also known how variations in the proportions between the concentrations of fluorophores present on the retina can be indicative of some disorders of the eye, such as Age-Related Macular Degeneration (AMD) and the Diabetic Retinopathy (DR).

In the field of ophthalmology, techniques are known for selectively measuring the concentration of fluorophores present on the retina by means of spectral analysis of fluorescence images of the retina.

Typically, these techniques consist of dividing the light emission band of the fluorophores into wavelength intervals, separately acquiring the light emitted by the fluorophores in these wavelength bands and calculating the concentrations of fluorophores present on the retina based on the light emission spectra of these latter.

Numerous examples of ophthalmic machines are known arranged to acquire fluorescence images of the retina and calculate, based on the aforesaid images, the concentrations of fluorophores present on the retina.

One example of these devices consists of the ophthalmic machine described in the article "Ocular fundus auto-fluorescence observations at different wavelengths in patients with age related macular degeneration and diabetic retinopathy"—Authors: Hammer et al; Published online: 26 Jul. 2007; Copyright Springer-Verlag 2007.

The ophthalmic machine described in the aforesaid article is arranged to provide images of the retina with different spectral content and recombine these images to obtain a color fluorescence image of the retina.

In particular, it consists of a fundus camera arranged so as to illuminate the retina with an excitation light having wavelengths comprised between 475-515 nm. The fluorescence light emitted by the retina is sent directly, without any preliminary filtering, to two band-pass filters having passing bands of 530-570 nm and 570-675 nm. These band-pass filters act in parallel and select the light having wavelengths comprised in the respective passing bands. The light filtered and transmitted by the band-pass filters is subsequently received by two separate CCD sensors.

The ophthalmic machine described in the aforesaid article has some drawbacks.

In general, the images of the retina provided by it are greatly disturbed by the fluorescence of the lens of the eye. As is clearly understood from the text of the aforesaid article, the ophthalmic machine can only be used in a satisfactory manner on patients in which the natural lens has been replaced with an artificial lens.

Another drawback consists in the fact that the ophthalmic machine uses an excitation light with wavelengths of 475-515 nm to excite the fluorophores of the retina. This excitation light excites the fluorophores of the retina inefficiently, with emission peaks in the green region of the spectrum, for example AGE (Advanced Glycation End-products) and FAD (Oxidized Flavinadenin Dinucleotide) fluorophores.

A further drawback consists in the fact that the ophthalmic machine uses a narrow spectrum (530-675 nm) to filter the fluorescence light produced by the fluorophores. Therefore, it is capable of offering high performance in the detection of fluorescence light produced by the Lipofuscin fluorophore (with emission peak around 600 nm) but it is not particularly efficient in detecting the light produced by fluorescence of the AGE and FAD fluorophores (emission peaks in the region of 500 nm).

From the above, it is evident how the machine described in the aforesaid article offers unsatisfactory performance in the detection of local variations in the concentration of AGE and FAD fluorophores. This constitutes a considerable limitation given that, as known from the literature, local variations in the concentration of these fluorophores on the retina can be correlated to the presence of diseases such as AMD and RD.

The machine described in the aforesaid article is also very costly, given that division of the light emitted by the retina into different bands of wavelengths is implemented by means of multiple special filters for fluorescence, with very high optical density, typically greater than 6 in the related blocking band.

The article "Identification of Amyloid Plaques in Retinas from Alzheimer's Patients and Noninvasive In Vivo Optical Imaging of Retinal Plaques in a Mouse Model"—Authors: Maya Koronyo-Hamaoui et al.—Published: NeuroImage, Jun. 13, 2010, pp. 5204-5217, 54, Elsevier Inc., presents a study on human patients and on laboratory animals that shows the correlation between Alzheimer's disease, the presence of beta-amyloid plaques in the brain and the presence of beta-amyloid plaques on the retina.

The same article presents some methods of detecting amyloid plaques by means of staining with fluorescent substances, among which curcumin.

The same information is also available in the patent US2011/0286932 A1.

Detection of the beta-amyloid plaques (typically very small in dimension, in the order of around 1-5 micron) is easily performed in-vitro, after the death of the patient, by means of confocal fluorescent microscopy.

To obtain a reliable diagnosis with a living patient, by means of "imaging" techniques of the retina, the use of conventional apparatus for inspecting the ocular fundus is somewhat problematic due to the insufficient optical resolution (10-20 micron) of these devices. At the state of the art, several examples of ophthalmic machines have been proposed for identifying beta-amyloid plaques on the retina in vivo.

The U.S. Pat. No. 9,149,184B2 describes an ophthalmic machine capable of providing images, filmed with a broad optical field, of the retina of subjects having taken a fluorescent substance to stain possible beta-amyloid plaques.

Following an initial rough evaluation of the areas in which the presence of beta-amyloid plaques is suspected, the machine is capable of optical zooming to acquire further images with a smaller field and with a higher resolution in said areas.

The U.S. Pat. No. 9,320,436B2 describes an ophthalmic machine that detects beta-amyloid plaques in individual layers of the retina, using various techniques, also including OCT (Optical Coherence Tomography) imaging techniques.

The patent application WO2014151573A1 describes an ophthalmic machine that provides images of the retina, using retro mode illumination, in combination with images acquired with other techniques.

Finally, ophthalmic machines are known that are provided with adaptive optics to provide high resolution images of the retina so as to allow identification of beta-amyloid plaques. The main aim of the present invention is to provide an ophthalmic machine capable of providing images of the retina, in particular fluorescence images of the retina, that allows the drawbacks of the prior art, indicated above, to be overcome.

Within this aim, an object of the present invention is to provide an ophthalmic machine that allows the acquisition of fluorescence images of the retina such as to permit the identification of local variations of proportion between the various fluorophores present on the retina, in particular Lipofuscin (especially the component A2E of Lipofuscin), AGE and FAD.

A further object of the present invention is to provide an ophthalmic machine that allows the acquisition of fluorescence images of the retina such as to permit the detection of beta-amyloid plaques present on the retina, even if very small in dimension (for example below 5 micron).

A further object of the present invention is to provide an ophthalmic machine that allows the acquisition of fluorescence images of the retina that are substantially exempt from possible optical disturbances caused by fluorescence of the lens.

A further object of the present invention is to provide an ophthalmic machine that is easy to produce on an industrial scale, at competitive costs.

This aim and these objects, together with other objects that will be more apparent from the subsequent description and from the accompanying drawings, are achieved according to the invention, by an ophthalmic machine according to claim 1 and to the related dependent claims appended below.

Figure 2:
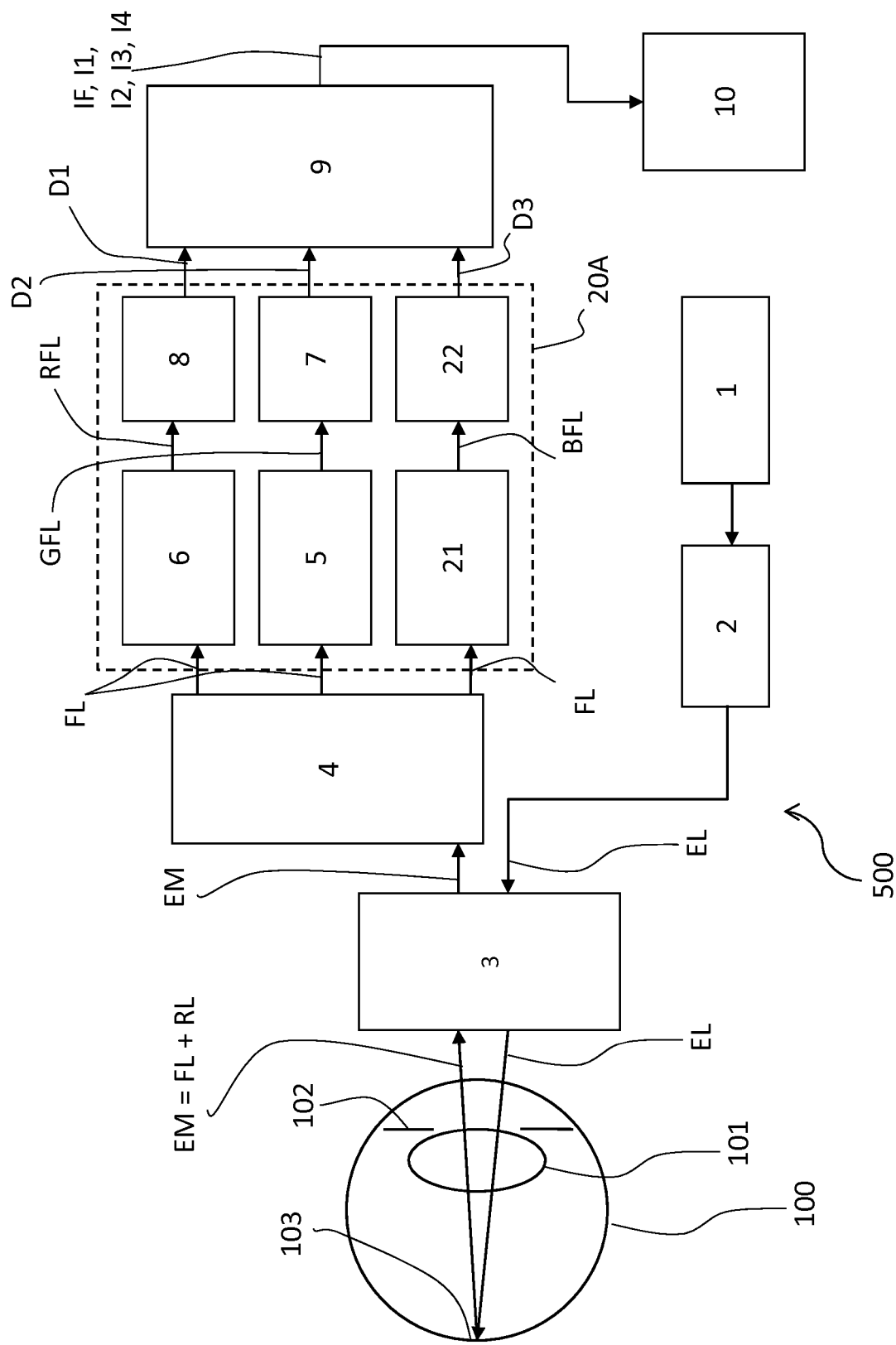
Figure 3:
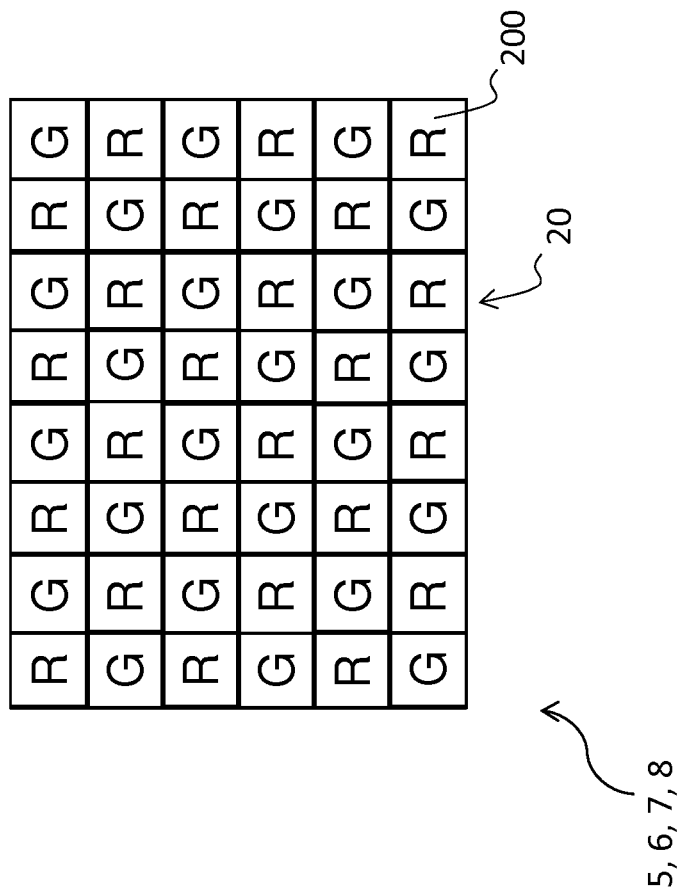

Further characteristics and advantages of the ophthalmic machine according to the invention will be more apparent with reference to the description given below and to the accompanying figures, provided purely for explanatory and non-limiting purposes, wherein:

FIG. 1 schematically shows the ophthalmic machine according to the invention, in an embodiment thereof;

FIG. 2 schematically shows the ophthalmic machine according to the invention, in a further embodiment thereof;

FIGS. 3 and 4 show some possible examples of embodiments of parts of the ophthalmic machine according to the invention.

With reference to FIG. 1, the present invention relates to an ophthalmic machine 500 for acquiring images of the retina, in particular color fluorescence images of the retina. The term color fluorescence image of the retina is intended as a color image showing the fluorescence light emitted by the retina with diverse wavelengths. In the aforesaid image, the light emitted with a certain wavelength is represented by pixels having a corresponding color. According to the invention, the ophthalmic machine 500 comprises lighting means adapted to produce a beam of excitation light EL with wavelengths comprised between 430 nm and 490 nm.

Preferably, the aforesaid lighting means comprise a light source 1 and an excitation filter 2. Preferably, the light source 1 comprises an LED light source.

The light emitted by the light source 1 is received and filtered by the excitation filter 2. This filter is advantageously arranged so as to receive and filter the light emitted by the light source 1 to transmit light with wavelengths comprised in the interval 430-490 nm.

Preferably, the excitation filter 2 comprises one or more optical filters capable of blocking possible spurious light with wavelengths outside the interval established for the wavelengths of the beam of excitation light EL.

The ophthalmic machine 500 comprises optical scanning means 3 adapted to scan the beam of excitation light EL on the retina 103 of an eye 100 of a subject (a human or, more generally, a mammal).

In particular, the scanning means 3 are adapted to receive the excitation light EL produced by the lighting means 1, 2 and to project, by performing an optical scan, the excitation light EL onto the retina 103.

The optical scanning means 3 can be any optical element or group of optical elements (also of known type) adapted to perform a unidirectional or bidirectional scan of a beam of light on the retina.

Preferably, the optical scanning means 3 are arranged so that the excitation light EL is projected as a light beam entering the eye at a first portion of the pupil 102 of the eye. When illuminated by the excitation light EL, the retina 103 emits a light EM that comprises reflected light RL, having the same wavelengths as the excitation light EL, and fluorescence light FL, produced by fluorophores present on the retina, having higher wavelengths with respect to the wavelengths of the excitation light EL.

The aforesaid fluorophores can be fluorophores naturally present on the retina, such as Lipofuscin, AGE and FAD fluorophores, or can be fluorescent substances given and transported to the retina through the bloodstream, such as curcumin or its derivatives. In the first case, the fluorescence light FL is an autofluorescence light emitted by the retina, while in the second case, the fluorescence light FL is a sum of the autofluorescence light and the light emitted by the fluorescent substances taken by the patient.

Preferably, the optical scanning means 3 are adapted to receive and transmit the light EM emitted by the retina, when this one is illuminated by the excitation light EL, performing an optical de-scanning.

Preferably, the optical scanning means 3 are arranged so that the light EM emitted by the retina is collected at a second portion of the pupil 102, separate from the first portion of pupil through which the excitation light EL passes.

Therefore, the excitation light EL and the light EM emitted by the retina pass through separate zones of the lens 101 of the eye 100. In this way, the fluorescence light FL emitted by the retina does not superimpose the light produced by fluorescence in the portion of lens illuminated by the excitation beam EL. This allows a drastic reduction of light disturbances caused by fluorescence of the lens, when illuminated by the excitation light EL.

As mentioned above, the light EM emitted by the retina comprises reflected light RL, having the same wavelengths as the excitation light EL, and fluorescence light FL, having higher wavelengths with respect to the excitation light EL.

The fluorescence light FL, produced by the retina, represents the useful signal to be used to provide fluorescence images of the retina, in particular color fluorescence images of the retina. The reflected light RL instead represents a disturbance capable of significantly worsening the quality of the fluorescence images of the retina to be acquired.

According to the invention, the ophthalmic machine 500 comprises first filtering means 4 adapted to receive and filter the light EM emitted by the retina, when illuminated by the excitation light EL.

The first filtering means 4 have a first blocking band BB1 arranged so as to block light RL with wavelengths corresponding to the wavelengths of the excitation light EL and a first passing band BP1 arranged so as to allow the transmission of light FL with wavelengths higher than the wavelengths of the excitation light EL.

The first filtering means 4 have an optical density (OD) greater than 6 (attenuation higher than $10^6$ times) in the first blocking band BB1.

Advantageously, the first filtering means 4 are arranged to block the reflected light RL and to select the fluorescence light FL from the light EM emitted by the retina.

Preferably, the filtering means 4 comprise a single barrier filter capable of blocking (attenuating it with attenuation higher than $10^6$ times) the light having wavelengths comprised in the blocking band BB1.

Preferably, this barrier is of the high-pass type with a cut-off wavelength slightly higher than the maximum wavelength established for the excitation light EL.

For example, in the case in which the maximum wavelength of the excitation light EL is 490 nm, the barrier filter could have a cut-off wavelength of 500 nm, therefore a blocking band BB1 in the interval of wavelengths lower than 500 nm and a passing band BP1 in the interval of wavelengths higher than 500 nm.

According to the invention, the ophthalmic machine 500 comprises second filtering means 5 adapted to receive and filter the fluorescence light FL transmitted by the first filtering means 4.

The second filtering means 5 are arranged so as to select, in combination with the filtering means 4, the component corresponding roughly to the green wavelengths (green fluorescence light GFL) from the fluorescence light FL.

The second filtering means 5 have a second blocking band BB2 comprised in an interval of wavelengths higher than 600 nm and a second passing band BP2 comprised in an interval of wavelengths lower than 600 nm.

The second filtering means 5 have an optical density (OD) lower than 3 (attenuation lower than $10^3$ times) in the second blocking band BB2.

For example, in a possible embodiment, the second filtering means 5 can be of the low-pass filter type with cut-off wavelength in the region of 600 nm.

The filtering means 5 can also be of other types, for example band-pass with a second passing band BP2 comprised in the interval of wavelengths lower than 600 nm and at least a second blocking band BB2 comprised in the interval of wavelengths higher than 600 nm.

Preferably, the second filtering means 5 comprise a first matrix of micro-filters capable of receiving and filtering the fluorescence light FL transmitted by the filtering means 4. According to the invention, the ophthalmic machine 500 comprises third filtering means 6 adapted to receive and filter the light FL transmitted by the first filtering means 4. The third filtering means 6 are arranged so as to select the component corresponding roughly to the red wavelengths (red fluorescence light RFL) from the fluorescence light FL. The third filtering means 6 have a third blocking band BB3 comprised in an interval of wavelengths lower than 570 nm and a third passing band BP3 comprised in an interval of wavelengths higher than 570 nm.

The third filtering means 6 have an optical density (OD) lower than 3 (attenuation lower than $10^3$ times) in the third blocking band BB3.

For example, in a possible embodiment, the second filtering means 5 can be of the high-pass filter type with cut-off wavelength in the region of 570 nm.

The third filtering means 6 can also be of other types, for example band-pass, with a third passing band BP3 comprised in the interval of wavelengths higher than 570 nm and at least a third blocking band BB3 comprised in the interval of wavelengths lower than 570 nm.

Preferably, the third filtering means 6 comprise a second matrix of micro-filters capable of receiving and filtering the fluorescence light FL transmitted by the filtering means 4.

In a further example of embodiment, the filtering means 5 and 6 can be produced with a single optical element. This optical element can be a dichroic mirror with a cut-off wavelength comprised between 570 and 600 nm.

The dichroic mirror receives the fluorescence light FL and divides it into two bands of wavelengths, a band of wavelengths of the reflected light and a band of wavelengths of the transmitted light, the two bands being separated by a cut-off wavelength.

In the case in which it reflects light with wavelengths lower than the cut-off wavelength and transmits light with higher wavelengths, the dichroic mirror performs the function of the filtering means 5 through the reflection of light and the function of the filtering means 6 through the transmission of light.

In the case in which it transmits light with wavelengths lower than the cut-off wavelength and reflects light with higher wavelengths, the dichroic mirror performs the function of the filtering means 5 through the transmission of light and the function of the filtering means 6 through the reflection of light.

It is noted how the arrangement of the first filtering means 4, with high optical density (OD>6), in series with the filtering means 5, 6 allows significant relaxation of the attenuation requirements required for these latter. In fact, the filtering means 5, 6 can have a relatively low optical density (OD<3) in the respective blocking band BB2, BB3.

This allows a considerable reduction of costs with respect to prior art solutions that typically use high quality filters to select each component of the fluorescence light emitted by the retina.

According to the invention, the ophthalmic machine 500 comprises first detection means 7 adapted to receive the light GFL (green fluorescence light) transmitted by the second filtering means 5 and provide first detection signals D1 indicative of the light transmitted by said second filtering means.

Preferably, the first detection means 7 comprise a first matrix of photosensitive elements (for example CCD or C-MOS sensors) capable of receiving the green fluorescence light GFL, transmitted by the second filtering means 5, and providing the first detection signals D1.

According to the invention, the ophthalmic machine 500 comprises second detection means 8 adapted to receive the light RFL (red fluorescence light) transmitted by the third filtering means 6 and provide second detection signals D2 indicative of the light transmitted by said third filtering means.

Preferably, the second detection means 8 comprise a second matrix of photosensitive elements (for example CCD or C-MOS sensors) capable of receiving the red fluorescence light RFL, transmitted by the third filtering means 6, and providing the second detection signals D2.

In an example of embodiment, the first detection means 7 and the second detection means 8 can be separate CCD or CMOS sensors, which separately receive light transmitted by the filtering means 5 and 6.

According to the invention, the ophthalmic machine 500 comprises processing means 9 configured to receive the first and second detection signals D1, D2 provided by the first and second detection means 7, 8 and provide one or more images IF, I1, I2, I3, I4 of the retina. According to the invention, the images provided by the processing means 9 comprise at least a color fluorescence image IF of the retina.

The processing means 9 can, for example, consist of a computer capable of executing appropriate software instructions, stored on a storage medium, to process the detection signals provided by the filtering means and provide the aforesaid images of the retina.

As mentioned above, a color fluorescence image IF of the retina is a color image in which there is a correspondence between the colors that identify some areas of the retina and the wavelengths of the fluorescence light FL coming from these portions of retina.

Preferably, but not necessarily, there is a correspondence between the color with which some areas of the retina are represented in the color fluorescence image IF and the color of the fluorescence light emitted by these portions of retina.

For example, it is preferable for the areas of the retina represented in green or red in the color fluorescence image IF to correspond to portions of retina that emit a green or red fluorescence light.

Naturally, solutions of different type are possible.

Preferably, the processing means 9 are adapted to provide at least an image of the retina selected among a ratiometric image I1 of the retina, a green fluorescence image I2 of the retina, a red fluorescence image I3 and a mono-chromatic fluorescence image I4 of the retina, for example by processing a color fluorescence image IF of the retina, already produced and stored and/or the detection signals used to obtain this image.

A ratiometric image I1 of the retina is a mono-chromatic image in which the pixel levels are indicative of the ratios between the intensity of the green fluorescence light GFL and the intensity of the red fluorescence light RFL emitted by the corresponding portions of retina. To produce a ratiometric image I1, the processing means 9 calculate the GFL/RFL ratio for the various areas of the retina based on the information (levels of colored pixels) provided by the color fluorescence image IF of the retina.

A ratiometric image I1 of the retina is particularly useful to highlight, by means of local variation of luminosity, the areas of the retina in which the GFL/RFL ratio differs with respect to the average of said ratio that characterizes the rest of the retina.

These local variations of the GFL/RFL ratio can be indicative of disorders of the retina. For example, in a ratiometric image of a retina affected by AMD, the central area of the retina is typically more luminous with respect to the other portions of retina (increase of the green fluorescence light with respect to the red fluorescence light emitted by the retina).

A green fluorescence image I2 of the retina is a mono-chromatic image in which the pixel levels are indicative of the intensity of the green fluorescence light GFL emitted by the corresponding areas of the retina.

The processing means 9 calculate the pixel levels of the green fluorescence image I2 based on the green pixel levels of the color fluorescence image IF of the retina (if necessary directly based on the detection signals that have been processed to provide this image).

A green fluorescence image I2 of the retina is particularly useful to highlight the areas of the retina in which the intensity of the green fluorescence light, as detected, differs with respect to the average intensity of the green fluorescence light emitted by the rest of the retina. These local variations of the quantity of green fluorescence light GFL can be indicative of disorders of the retina.

For example, possible lesions of the retinal pigment epithelium (RPE) can be shown in a green fluorescence image I2 as areas with high luminosity (high emission of green fluorescence light by the exposed Bruch's membrane collagen due to the aforesaid lesions).

As further example, local variations of the quantity of green fluorescence light GFL emitted can be identified in green fluorescence images I2 of retinas affected by AMD and RD (local increase of the concentration of AGE and FAD fluorophores).

A red fluorescence image I3 of the retina is a mono-chromatic image in which the pixel levels are indicative of the intensity of the red fluorescence light RFL emitted by the corresponding areas of the retina.

The processing means 9 calculate the pixel levels of the red fluorescence image I3 based on the red pixel levels of the color fluorescence image IF of the retina and/or based directly on the detection signals that have been processed to provide this image.

A red fluorescence image I3 of the retina is particularly useful for highlighting the areas of the retina at which the intensity of the red fluorescence light, as detected, differs from the average intensity of the red fluorescence light emitted by the rest of the retina.

These local variations of the quantity of red fluorescence light RFL can be indicative of disorders of the retina.

For example, in a red fluorescence image I3 of a retina affected by Geographic Atrophy (GA), the portions of retina in which the photo-receivers (cones and rods) are inactive appear typically darker with respect to the rest of the retina (decrease of the local concentration of Lipofuscin, i.e. of the metabolite normally produced by the photo-receivers).

As further example, in red fluorescence images I3 of retinas affected by AMD, local increases of the concentration of Lipofuscin fluorophore can be identified (insufficient disposal of this metabolic product due to local blood flow deficits).

A mono-chromatic fluorescence image I4 of the retina is a mono-chromatic image in which the pixel levels are indicative of the total intensity of the fluorescence light FL emitted by the corresponding areas of the retina.

In practice, this image corresponds to a typical fluorescence image of the retina already provided by prior art ophthalmic machines, using a blue excitation light.

The processing means 9 calculate the pixel levels of the mono-chromatic fluorescence image I4 based on the levels of all the pixels of the color fluorescence image IF of the retina and/or directly based on the detection signals that have been processed to provide this image. A mono-chromatic fluorescence image I4 of the retina is useful to identify some disorders of the retina, for example AMD or RD.

Preferably, the ophthalmic machine 500 comprises a user interface 10 (for example a monitor) on which the images of the retina IF, I1, I2, I3, I4 provided by the processing means 9 can be viewed.

In an embodiment of the invention, the ophthalmic machine 500 comprises a sensor element 20 advantageously arranged so as to produce the second and third filtering means 5, 6 and the first and second detection means 7, 8 (FIG. 3).

Preferably, the first matrix of micro-filters 5, which forms the aforesaid second filtering means, and the first matrix of photosensitive elements 7, which forms the aforesaid first detection means, are operatively associated to one another so that each micro-filter of the first matrix of micro-filters 5 is operatively associated to (for example superimposed on) a corresponding photosensitive element of the first matrix of photosensitive elements 7. Preferably, the second matrix of micro-filters 6, which forms the aforesaid third filtering means, and the second matrix of photosensitive elements 8, which forms the aforesaid second detection means, are operatively associated to one another so that each micro-filter of the second matrix of micro-filters 6 is operatively associated to (for example superimposed on) a corresponding photosensitive element of the second matrix of photosensitive elements 8.

In particular, the sensor element 20 comprises the first and second matrix of micro-filters 5, 6 and the first and second matrix of photosensitive elements 7, 8, operatively associated to one another, as illustrated above.

Preferably, the sensor element 20 comprises first filtering and detection groups G, each of which comprises a micro-filter of the first matrix of micro-filters 5 and a photosensitive element of the first matrix of photosensitive elements 7, operatively associated to (for example superimposed on) one another.

Preferably, the sensor element 20 comprises second filtering and detection groups R, each of which comprises a micro-filter of the second matrix of micro-filters 6 and a photosensitive element of the second matrix of photosensitive elements 8, operatively associated to (for example superimposed on) one another.

Preferably, the first and second filtering and detection groups G, R are arranged interlaced on a receiving surface 200 of the sensor element 20. Two possible preferred modes of interlacing are shown in FIGS. 3 and 4.

This solution allows the acquisition of the green fluorescence light GFL and the red fluorescence light RFL emitted by the retina in a simple and inexpensive manner, using a single optics (not shown) that optically conjugates the retina 103 and the receiving surface 200 of the sensor element 20.

Preferably, the sensor element 20 is a Bayer matrix sensor, commonly available commercially (FIG. 4) and of which only the green and red filtering and detection groups are used. According to an embodiment of the invention, the lighting means 1, 2 of the ophthalmic machine 500 are adapted to produce an excitation light EL having wavelengths comprised between 430 nm and 450 nm and the first filtering means 4 of the ophthalmic machine 500 have a first blocking band BB1 to block light with wavelengths lower than or equal to 460 nm.

The use of lighting means 1, 2 capable of projecting an excitation light with shorter wavelengths comprised in a narrow interval facilitates the subsequent division of the wavelengths of the fluorescence light FL emitted by the retina into three bands of wavelengths (instead of two), increasing the performance of the machine without significant increases in cost.

In fact, according to the aforesaid embodiment, the ophthalmic machine 500 comprises fourth filtering means 21 adapted to receive and filter the light FL transmitted by the first filtering means 4.

The fourth filtering means 21 are arranged so as to select, in combination with the first filtering means 4, the component corresponding to the blue wavelengths (blue fluorescence light BFL), with wavelengths corresponding to those comprised in the fourth passing band BP4, from the fluorescence light FL, produced by the fluorophores present on the retina.

The fourth filtering means 21 have a fourth blocking band BB4 comprised in an interval of wavelengths higher than around 500 nm and a fourth passing band BP4 comprised in an interval of wavelengths lower than around 500 nm.

The fourth filtering means 21 have an optical density (OD) lower than 3 (attenuation lower than $10^3$ times) in the fourth blocking band BB4.

For example, in a possible embodiment, the fourth filtering means 21 are of the low-pass type with cut-off wavelength in the region of 500 nm.

In another embodiment, the filtering means 21 can be of band-pass type, having a fourth passing band BP4 comprised in the interval of wavelengths lower than 500 nm and at least a fourth blocking band BB4 comprised in the interval of wavelengths higher than 500 nm. Preferably, the fourth filtering means 21 comprise a third matrix of micro-filters capable of receiving and filtering the fluorescence light FL, transmitted by the filtering means 4, at a suitable receiving surface.

According to the aforesaid embodiment, the ophthalmic machine 500 comprises third detection means 22 adapted to receive the light BFL (blue fluorescence light) transmitted by the fourth filtering means 21 and provide third detection signals D3 indicative of the light transmitted by said fourth filtering means.

Preferably, the third detection means 22 comprise a third matrix of photosensitive elements (for example CCD or C-MOS sensors) capable of receiving the blue fluorescence light BFL, transmitted by the fourth filtering means 21 and providing the third detection signals D3.

Preferably, the third matrix of micro-filters 21, which forms the aforesaid fourth filtering means, and the third matrix of photosensitive elements 22, which forms the aforesaid third detection means, are operatively associated to one another so that each micro-filter of the third matrix of micro-filters 21 is operatively associated to (for example superimposed on) a corresponding photosensitive element of the third matrix of photosensitive elements 22.

Moreover, according to the aforesaid embodiment, the processing means 9 are configured to receive the first, second and third detection signals D1, D2, D3 provided by the first, second and third detection means 7, 8, 22 and provide one or more images IF, I1, I2, I3, I4 of the retina. The images provided by the processing means 9 comprise at least a color fluorescence image IF of the retina.

Preferably, the ophthalmic machine 500 comprises a sensor element 20A arranged so as to comprise the second, third and fourth filtering means 5, 6, 21 and the first, second and third detection means 7, 8, 22 (FIG. 4).

In particular, the sensor element 20A comprises the first, second and third matrix of micro-filters 5, 6, 21 and the first, second and third matrix of photosensitive elements 7, 8, 21 operatively associated to one another as illustrated above.

Preferably, the sensor element 20A comprises first filtering and detection groups G, each of which comprises a micro-filter of the first matrix of micro-filters 5 and a photosensitive element of the first matrix of photosensitive elements 7, operatively associated to (for example superimposed on) one another.

Preferably, the sensor element 20A comprises second filtering and detection groups R, each of which comprises a micro-filter of the second matrix of micro-filters 6 and a photosensitive element of the second matrix of photosensitive elements 8, operatively associated to (for example superimposed on) one another.

Preferably, the sensor element 20A comprises third filtering and detection groups B, each of which comprises a micro-filter of the third matrix of micro-filters 21 and a photosensitive element of the third matrix of photosensitive elements 22, operatively associated to (for example superimposed on) one another.

Preferably, the first, second and third filtering and detection groups G, R, B are arranged interlaced, on a receiving surface 200A of the sensor element 20A.

This solution allows the acquisition of the green fluorescence light GFL, the red fluorescence light RFL and the blue fluorescence light BFL emitted by the retina in a simple and inexpensive manner, using a single optics (not shown) that optically conjugates the retina 103 and the receiving surface 200A of the sensor element 20A.

Preferably, the sensor element 20A is a Bayer matrix sensor, commonly available commercially (FIG. 4).

The ophthalmic machine 500 is particularly suitable as instrumental support in the diagnosis of some diseases of the retina and of some neurodegenerative diseases.

It offers significant advantages in identification of possible disorders of the retina and/or possible neurodegenerative diseases (such as Alzheimer's disease) with respect to conventional devices.

Some examples of methods of use of the ophthalmic machine 500 are illustrated below.

EXAMPLE #1

In a first example, the ophthalmic machine 500 can be used to diagnose a disease of the retina of a subject (a human or, more generally, a mammal).

The ophthalmic machine 500 provides at least a color fluorescence image IF of the retina of a subject.

The color fluorescence image IF of the retina is analyzed in order to identify the distribution of intensity and color of the fluorescence light emitted by the various portions of retina and the shape and dimensions of the aforesaid portions of retina.

The color fluorescence image IF of the retina can be shown to a human operator on the monitor 10 for visual analysis or can be analyzed by the processing means 9 through specific software.

The color fluorescence image IF of the retina provides information that allows identification of portions of the retina with a suspected disorder, for example through the detection of local variations of intensity and color of the fluorescence light emitted with respect to the average intensity and color of the fluorescence light emitted by the rest of the retina.

The color fluorescence image IF of the retina also provides information (color, luminosity, shape, dimension, number or variation of color or luminosity of the suspected portions of retina) that allows the disorder that might affect the suspected portions of retina to be identified.

The ophthalmic machine 500 is capable of providing a wide set of information useful for identifying disorders of the retina.

For example, portions of retina with suspected disorders can be identified in the color fluorescence image IF not only based on their shape or luminosity (as occurs in images provided by conventional ophthalmic machines), but also through the local variations of color of the fluorescence light emitted with respect to the average color of the fluorescence light emitted by the rest of the retina.

Therefore, the ophthalmic machine 500 allows a more accurate diagnosis of disorders of the retina and, possibly, early identification of these disorders, for example in cases in which the disorder has determined local variations of color of the fluorescence light emitted with respect to the average color of the fluorescence light emitted by the rest of the retina but there are still no variations of intensity of the fluorescence light emitted, with respect to the average intensity of the fluorescence light emitted by the rest of the retina.

It must be noted that early identification of the disorder is particularly important for the treatment of some diseases of the retina, such as AMD and RD, to ensure an acceptable quality of life for the patient.

The ophthalmic machine 500 can be used in a method of diagnosing a disease of the retina (for example AMD or RD) of a subject (a human or, more generally, a mammal) that includes the following steps:

acquiring, by means of the ophthalmic machine 500, a color fluorescence image IF of the retina of the subject;

analyzing said fluorescence image IF to identify portions of retina subject to a medical condition.

Analysis of the fluorescence image IF can, for example, comprise the identification of portions of retina with local variations of color of the fluorescence light emitted with respect to the average color of the fluorescence light emitted by the rest of the retina and/or with local variation of intensity of the fluorescence light emitted, with respect to the average intensity of the fluorescence light emitted by the rest of the retina.

EXAMPLE #2

In a second example, the ophthalmic machine 500 can be used to diagnose a disease of the retina of a subject (a human or, more generally, a mammal).

The ophthalmic machine 500 provides a color fluorescence image IF of the retina of said subject.

The ophthalmic machine 500 processes the color fluorescence image IF of the retina acquired and stored and/or processes the aforesaid detection signals D1, D2, D3 indicative of the fluorescence light in the various bands of wavelengths coming from the retina.

Following this processing, the ophthalmic machine 500 provides at least a further image, selected among a ratiometric image I1 of the retina, a green fluorescence image I2 of the retina, a red fluorescence image I3 of the retina and a mono-chromatic fluorescence image I4 of the retina.

The ophthalmic machine 500 is capable of providing a wide set of information useful for identifying possible disorders of the retina.

Analysis of the color fluorescence image IF together with at least one of the images I1, I2, I3, I4 listed above, allows easier and more reliable diagnosis of a disease of the retina with respect to conventional methods that only use monochromatic fluorescence images.

The combination of differentiated types of information allows a significant reduction in the risk of diagnostic error and, in other cases, can effectively contribute to an early diagnosis of a possible medical condition.

The ophthalmic machine 500 can be used in a method for diagnosing a disease of the retina (for example AMD or RD) of a subject (a human or, more generally, a mammal) that includes the following steps:

acquiring, by means of the ophthalmic machine 500, a color fluorescence image IF of the retina of the subject;

acquiring, by means of the ophthalmic machine 500, at least a further image, selected among a ratiometric image I1 of the retina, a green fluorescence image I2 of the retina, a red fluorescence image I3 of the retina and a mono-chromatic fluorescence image I4 of the retina;

analyzing said fluorescence image IF and said at least a further image to identify portions of retina subject to a medical condition.

Analysis of these images can, for example, comprise identification of portions of retina with local variations of color of the fluorescence light emitted with respect to the average color of the fluorescence light emitted by the rest of the retina and/or with local variations of intensity of the fluorescence light emitted, with respect to the average intensity of the fluorescence light emitted by the rest of the retina.

EXAMPLE #3

In a third example, the ophthalmic machine 500 can be used to diagnose neurodegenerative diseases (such as Alzheimer's disease) of a subject (a human or, more generally, a mammal) having taken a fluorescent substance.

The ophthalmic machine 500 provides a color fluorescence image IF of the retina of the subject.

The color fluorescence image IF of the retina is analyzed in order to identify local variations of intensity and color of the fluorescence light emitted by the various portions of retina with respect to the average intensity and color of the fluorescence light emitted by the rest of the retina and the shape and dimensions of the aforesaid portions of retina.

The color fluorescence image IF of the retina can be shown to a human operator on the monitor 10 for visual analysis or can be analyzed by the processing means 9 through specific software.

The ophthalmic machine 500 offers significant advantages for the identification of possible neurodegenerative diseases of the subject with respect to conventional devices.

For example, to diagnose Alzheimer's disease, the fluorescent substance to be taken by the patient can be curcumin or derivatives thereof.

As is known, this substance binds to the beta-amyloid plaques present on the retinal fiber nerve layer and retinal ganglion cells.

Moreover, curcumin and derivatives thereof are characterized by emission peaks in the interval of wavelengths lower than 550 nm, substantially different with respect to that of Lipofuscin (fluorophore that dominates the retina with emission peak around 600 nm). Therefore, curcumin or derivatives thereof emit a green fluorescence light that differs significantly from the red or orange fluorescence light normally emitted by Lipofuscin. In this way, in the presence of Alzheimer's disease, a color fluorescence image IF of the retina allows easy identification of the beta-amyloid plaques stained with the fluorescent substance given.

The beta-amyloid plaques, even if very small in dimension, are in fact easily identifiable (with high degree of accuracy) on the color fluorescence image as small stains colored differently with respect to the average color of the retina.

The ophthalmic machine 500 can be used in a method of diagnosing a neurodegenerative disease (such as Alzheimer's disease) of a subject (a human or, more generally, a mammal) that includes the following steps:
   having the subject take a fluorescent substance (such as curcumin or derivatives thereof);
   acquiring, by means of the ophthalmic machine 500, a color fluorescence image IF of the retina of the subject;
   analyzing said fluorescence image IF to identify the presence of beta-amyloid plaques on the retina.

Analysis of the fluorescence image IF can, for example, comprise the identification of portions of retina with local variations of color of the fluorescence light emitted with respect to the average color of the fluorescence light emitted by the rest of the retina and/or with local variations of intensity of the fluorescence light emitted, with respect to the average intensity of the fluorescence light emitted by the rest of the retina.

EXAMPLE #4

In a fourth example, the ophthalmic machine 500 can be used to diagnose a neurodegenerative disease (such as Alzheimer's disease) of a subject (a human or, more generally, a mammal) having taken a fluorescent substance.

The ophthalmic machine 500 provides a color fluorescence image IF of the retina of said subject after having taken the fluorescent substance.

The ophthalmic machine 500 processes the color fluorescence image IF of the retina acquired and stored and/or processes the aforesaid detection signals D1, D2, D3 indicative of the fluorescence light in the various bands of wavelengths coming from the retina.

Following this processing, the ophthalmic machine 500 provides at least a further image, selected among a color fluorescence image IF of the retina, a ratiometric image I1 of the retina, a green fluorescence image I2 of the retina, a red fluorescence image I3 of the retina and a mono-chromatic fluorescence image I4 of the retina.

In this way, the ophthalmic machine 500 is capable of providing a wide set of information useful for identifying possible neurodegenerative diseases of the subject.

Analysis of the color fluorescence image together with at least one of the images listed above allows easier and more reliable identification of the presence of the beta-amyloid plaques on the retina with respect to the conventional methods that only use mono-chromatic fluorescence images.

The combination of differentiated types of information allows a significant reduction in the risk of diagnostic error and, in other cases, can effectively contribute to an early diagnosis of a possible medical condition. The ophthalmic machine 500 can be used in a method of diagnosing a disease of the retina (for example AMD or RD) of a subject (a human or, more generally, a mammal) that includes the following steps:
   having the subject take a fluorescent substance (such as curcumin or derivatives thereof);
   acquiring, by means of the ophthalmic machine 500, a color fluorescence image IF of the retina of the subject;
   acquiring, by means of the ophthalmic machine 500, at least a further image, selected among a ratiometric image I1 of the retina, a green fluorescence image I2 of the retina, a red fluorescence image I3 of the retina and a mono-chromatic fluorescence image I4 of the retina;
   analyzing said fluorescence image IF and said at least one further image to identify the presence of beta-amyloid plaques on the retina.

Analysis of these images can comprise, for example, identification of portions of retina with local variations of color of the fluorescence light emitted with respect to the average color of the fluorescence light emitted by the rest of the retina and/or with local variations of intensity of the fluorescence light emitted, with respect to the average intensity of the fluorescence light emitted by the rest of the retina.

The ophthalmic machine 500 also has numerous advantages of a constructive and/or functional nature with respect to prior art devices.

The use of the scanning means 3, arranged as illustrated above, allows a significant reduction of the light disturbances caused by fluorescence of the lens of the eye.

The use of a single high-quality barrier filter (filtering means 4) with OD>6 in the blocking band reduces the production costs of the machine.

The use of low quality filtering means 5, 6 and 21 with OD<3 in the corresponding blocking bands to divide the whole band of fluorescence light into partial bands further reduces the production costs of the machine.

The production of filtering means 5, 6, 21 and of detection means 7, 8, 22 as matrices of micro-filters and matrices of photosensitive elements operatively associated to (for example superimposed on) one another, allows significant simplification of the optics of the machine, with consequent reduction in production costs.

The implementation of the matrices of micro-filters 5, 6, 21 and of the matrices of photosensitive elements 7, 8, 22 by means of a Bayer matrix sensor (commercially available) allows a further reduction in the production costs of the ophthalmic machine.

The ophthalmic machine 500 has a very compact structure and is easy to produce on an industrial scale, with considerable advantages in terms of limiting production costs.

The invention claimed is:

1. An ophthalmic machine comprising:
   lighting means adapted to provide an excitation light having wavelengths comprised between 430 nm and 490 nm;
   scanning means adapted to scan said excitation light on an eye retina;
   first filtering means adapted to receive light emitted by the retina, when illuminated by said excitation light, said first filtering means having a first blocking band to block light with wavelengths corresponding to the wavelengths of said excitation light and a first passing band to transmit light with wavelengths higher than the wavelengths of said excitation light, said first filtering means having an optical density higher than 6 in said first blocking band;
   second filtering means adapted to receive the light transmitted by said first filtering means, said second filtering means having a second blocking band comprised in an interval of wavelengths higher than 600 nm and a second passing band comprised in an interval of wavelengths lower than 600 nm, said second filtering means having an optical density lower than 3 in said second blocking band;
   third filtering means adapted to receive the light transmitted by said first filtering means, said third filtering means having a third blocking band comprised in an interval of wavelengths lower than 570 nm and a third passing band comprised in an interval of wavelengths higher than 570 nm, said third filtering means having an optical density lower than 3 in said third blocking band;
   first detection means adapted to receive a light transmitted by said second filtering means and provide first detection signals indicative of the light transmitted by said second filtering means;
   second detection means adapted to receive a light transmitted by said third filtering means and provide second detection signals indicative of the light transmitted by said third filtering means; and
   processing means adapted to receive the first and second detection signals provided by said first and second detection means and provide one or more images of the retina, said one or more images of the retina comprising at least a color fluorescence image of the retina.

2. The ophthalmic machine of claim 1, wherein:
   said second filtering means comprise a first matrix of micro-filters and said first detection means comprise a first matrix of photosensitive elements, each micro-filter of said first matrix of micro-filters being operatively associated to a corresponding photosensitive element of said first matrix of photosensitive elements;
   said third filtering means comprise a second matrix of micro-filters and said second detection means comprise a second matrix of photosensitive elements, each micro-filter of said second matrix of micro-filters being operatively associated to a corresponding photosensitive element of said second matrix of photosensitive elements.

3. The ophthalmic machine of claim 2, comprising a sensor element that comprises said first and second matrixes of micro-filters and said first and second matrixes of photosensitive elements, said sensor element further comprising:
   first filtering and detection groups, each comprising a micro-filter of said first matrix of micro-filters and a photosensitive element of said first matrix of photosensitive elements operatively associated one to another;
   second filtering and detection groups, each comprising a micro-filter of said second matrix of micro-filters and a photosensitive element of said second matrix of photosensitive elements operatively associated one to another;
   said first and second filtering and detection groups being arranged interlaced on a receiving surface of said sensor element.

4. The ophthalmic machine of claim 1, wherein said lighting means are adapted to provide an excitation light having wavelengths comprised between 430 nm and 450 nm and in that said first filtering means have a first blocking band to block light with wavelengths lower than 460 nm, said ophthalmic machine further comprising:
   fourth filtering means adapted to receive the light transmitted by said first filtering means, said fourth filtering means having a fourth blocking band comprised in an interval of wavelengths higher than 500 nm and a fourth passing band comprised in an interval of wavelengths lower than 500 nm, said fourth filtering means having an optical density lower than 3 in said fourth blocking band;
   third detection means adapted to receive a light transmitted by said fourth filtering means and provide third detection signals indicative of the light transmitted by said fourth filtering means; and
   said processing means being adapted to receive the first, second and third detection signals provided by said first, second and third detection means and provide the one or more images of the retina based on the first, second and third detection signals.

5. The ophthalmic machine of claim 4, wherein said fourth filtering means comprise a third matrix of micro-filters and said third detection means comprise a third matrix of photosensitive elements, each micro-filter of said third matrix of micro-filters being operatively associated to a corresponding photosensitive element of said third matrix of photosensitive elements.

6. The ophthalmic machine of claim 5, wherein said sensor element comprises said first, second and third matrixes of micro-filters and said first, second and third matrixes of photosensitive elements, said sensor element comprising:

first filtering and detection groups, each comprising a micro-filter of said first matrix of micro-filters and a photosensitive element of said first matrix of photosensitive elements operatively associated one to another;

second filtering and detection groups, each comprising a micro-filter of said second matrix of micro-filters and a photosensitive element of said second matrix of photosensitive elements operatively associated one to another;

third filtering and detection groups, each comprising a micro-filter of said third matrix of micro-filters and a photosensitive element of said third matrix of photosensitive elements operatively associated one to another;

said first, second and third filtering and detection groups being arranged interlaced on a receiving surface of said sensor element.

7. The ophthalmic machine of claim 1, wherein said processing means are adapted to provide at least a further image of the retina selected among a ratiometric image of the retina, a green fluorescence image of the retina, a red fluorescence image of the retina and a mono-chromatic fluorescence image of the retina.

8. A diagnostic method using an ophthalmic machine, the method comprising:

scanning an excitation light on an eye retina of a subject, said excitation light having wavelengths comprised between 430 nm and 490 nm;

receiving light emitted by the retina when illuminated by said excitation light, via first filtering means having a first blocking band to block light with wavelengths corresponding to the wavelengths of said excitation light and a first passing band to transmit light with wavelengths higher than the wavelengths of said excitation light, said first filtering means having an optical density higher than 6 in said first blocking band;

receiving the light transmitted by said first filtering means via second filtering means having a second blocking band comprised in an interval of wavelengths higher than 600 nm and a second passing band comprised in an interval of wavelengths lower than 600 nm, said second filtering means having an optical density lower than 3 in said second blocking band;

receiving the light transmitted by said first filtering means via third filtering means having a third blocking band comprised in an interval of wavelengths lower than 570 nm and a third passing band comprised in an interval of wavelengths higher than 570 nm, said third filtering means having an optical density lower than 3 in said third blocking band;

receiving a light transmitted by said second filtering means and providing first detection signals indicative of the light transmitted by said second filtering means;

receiving a light transmitted by said third filtering means and providing second detection signals indicative of the light transmitted by said third filtering means; and receiving the first and second detection signals and providing images of the retina comprising at least a first color fluorescence image of the retina.

9. The diagnostic method of claim 8, further comprising analyzing the at least first color fluorescence image of the retina to identify one or more portions of the retina subject to a medical condition.

10. The diagnostic method of claim 9, wherein the analyzing the at least first color fluorescence image of the retina to identify one or more portions of the retina subject to a medical condition comprises:

identifying one or more portions of the retina with local variation of color of light emitted with respect to an average color of light emitted by the rest of the retina and/or with local variation of intensity of the light emitted with respect to an average intensity of the light emitted by the rest of the retina.

11. The diagnostic method of claim 8, wherein the provided images of the retina comprise at least a further image the retina selected among a ratiometric image of the retina, a green fluorescence image of the retina, a red fluorescence image of the retina and a mono-chromatic fluorescence image of the retina.

12. The diagnostic method of claim 11, further comprising analyzing the at least first color fluorescence image of the retina to identify one or more portions of the retina subject to a medical condition.

13. The diagnostic method of claim 8, further comprising:

obtaining the first color fluorescence image of the retina upon the subject having taken a fluorescent substance; and analyzing the first color fluorescence image to identify a presence of beta-amyloid plaques on the retina.

14. The diagnostic method of claim 13, comprising:

obtaining at least a further image of the retina upon the subject having taken the fluorescent substance, the at least further image selected among a ratiometric image of the retina, a green fluorescence image of the retina, a red fluorescence image of the retina and a mono-chromatic fluorescence image of the retina; and wherein the analyzing comprises analyzing the first color fluorescence image and the at least a further image of the retina to identify a presence of beta-amyloid plaques on the retina.

15. The diagnostic method of claim 8, wherein said excitation light have wavelengths comprised between 430 nm and 450 nm, and said first filtering means have a first blocking band to block light with wavelengths lower than 460 nm, the method further comprising:

receiving the light transmitted by said first filtering means via fourth filtering means having a fourth blocking band comprised in an interval of wavelengths higher than 500 nm and a fourth passing band comprised in an interval of wavelengths lower than 500 nm, said fourth filtering means having an optical density lower than 3 in said fourth blocking band;

receiving a light transmitted by said fourth filtering means and providing third detection signals indicative of the light transmitted by said fourth filtering means; and receiving the first, second and third detection signals provided by said first, second and third detection means and providing the images of the retina based on the first, second and third detection signals.

* * * * *